(12) United States Patent
Cox et al.

(10) Patent No.: US 10,722,435 B2
(45) Date of Patent: Jul. 28, 2020

(54) DEODORANT PRODUCTS

(71) Applicant: Conopco, Inc., Englewood Cliffs, NJ (US)

(72) Inventors: Diana Sheila Cox, Sharnbrook (GB); Alexander Gordon James, Sharnbrook (GB); Louise Ombler McMaster, Seacroft (GB); Joy Rachel McWalter, Seacroft (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/309,675

(22) PCT Filed: Jun. 13, 2017

(86) PCT No.: PCT/EP2017/064435
§ 371 (c)(1),
(2) Date: Dec. 13, 2018

(87) PCT Pub. No.: WO2017/216174
PCT Pub. Date: Dec. 21, 2017

(65) Prior Publication Data
US 2019/0125640 A1   May 2, 2019

(30) Foreign Application Priority Data

Jun. 17, 2016  (EP) .................................. 16174928

(51) Int. Cl.
| | | |
|---|---|---|
| *A61Q 15/00* | (2006.01) | |
| *A61K 8/34* | (2006.01) | |
| *A61K 8/37* | (2006.01) | |
| *A61K 8/891* | (2006.01) | |
| *A61K 8/33* | (2006.01) | |
| *A61K 8/04* | (2006.01) | |

(52) U.S. Cl.
CPC .............. *A61K 8/345* (2013.01); *A61K 8/046* (2013.01); *A61K 8/33* (2013.01); *A61K 8/347* (2013.01); *A61K 8/37* (2013.01); *A61K 8/891* (2013.01); *A61Q 15/00* (2013.01); *A61K 2800/30* (2013.01); *A61K 2800/56* (2013.01)

(58) Field of Classification Search
None
See application file for complete search history.

(56) References Cited

U.S. PATENT DOCUMENTS

| | | |
|---|---|---|
| 6,309,675 B1 | 10/2001 | Sobezak |
| 2006/0029624 A1 | 2/2006 | Banowski et al. |
| 2008/0187503 A1 | 8/2008 | Popoff et al. |
| 2008/0241089 A1 | 10/2008 | Banowski et al. |
| 2008/0241201 A1* | 10/2008 | Warr ....................... A61K 8/33 424/401 |
| 2009/0010864 A1 | 1/2009 | Banowski et al. |
| 2010/0047296 A1 | 2/2010 | Banowski et al. |
| 2012/0269876 A1* | 10/2012 | Satzinger ............. A61K 8/0241 424/401 |
| 2014/0169856 A1* | 6/2014 | Doering ................. A45D 40/00 401/55 |
| 2014/0322151 A1 | 10/2014 | Fricke et al. |

FOREIGN PATENT DOCUMENTS

| | | |
|---|---|---|
| DE | 10047759 | 10/2001 |
| DE | 102005029777 | 1/2007 |
| DE | 102011084155 | 7/2012 |
| DE | 102011086019 | 8/2012 |
| EP | 1576946 | 9/2005 |
| EP | 2114532 | 10/2011 |
| WO | WO0213776 | 2/2002 |
| WO | WO2006119981 | 11/2006 |
| WO | WO2007068339 | 6/2007 |
| WO | WO2007132439 | 11/2007 |
| WO | WO2010009977 | 4/2011 |
| WO | WO201210685 | 1/2012 |
| WO | WO2012084972 | 6/2012 |
| WO | WO2013092114 | 6/2013 |
| WO | WO2017216174 | 12/2017 |

OTHER PUBLICATIONS

Search Report and Written Opinion in PCTEP2017064435; dated Jul. 26, 2017.
24H Deodorant Body Spray; Mintel GNPD; 2016; pp. 1-2; XP002762616.
Search Report and Written Opinion in EP16174928; dated Oct. 21, 2016.

\* cited by examiner

*Primary Examiner* — Jeffrey T. Palenik
(74) *Attorney, Agent, or Firm* — Greenberg Traurig, LLP

(57) ABSTRACT

A deodorant composition comprising ethylhexylglycerol, triethyl citrate and BHT, wherein the ratio of ethylhexylglycerol to triethyl citrate is from 1:6 to 1:1 by weight and wherein the ratio of BHT to the sum of ethylhexylglycerol and triethyl citrate is from 1:40 to 1:5 by weight.

14 Claims, No Drawings

DEODORANT PRODUCTS

RELATED APPLICATIONS

The present application is a national phase filing under 35 USC 371 of International Application No. PCT/EP2017/064435, filed on Jun. 13, 2017, which claims the priority of European Patent Application No. 16174928.8, filed on Jun. 17, 2016, the entire contents of which are hereby incorporated by reference.

FIELD OF INVENTION

This invention relates to the field of deodorant compositions. In addition, this invention is concerned with achieving a deodorancy benefit upon the surface of the human body. The compositions and methods involved utilise anti-microbial deodorant actives. The compositions and methods of the invention are generally of greatest benefit when used on the most malodorous areas of the body, for example the underarm areas or feet.

BACKGROUND

Most anti-microbial and deodorant compositions reduce the number of viable microorganisms on the surface of the skin. It is well known that sweat is usually odourless until the skin microflora have degraded it. Typical deodorants include ethanol and triclosan (2,4,4'-trichloro,2'-hydroxydiphenyl ether) which is a well known anti-microbial agent. However, the deodorising effect obtained with such deodorants wears off with the passage of time and the microbiota progressively recover their numbers.

There is, therefore, a continuing requirement for effective and long lasting deodorant compositions on the market (particularly in the most malodorous areas, eg. the axillae).

DE 102011084155 (Henkel, 2012) discloses compositions suitable for use as deodorants and comprising multiple ingredients including triethyl citrate and, optionally, ethylhexylglycerol.

SUMMARY OF THE INVENTION

According to a first aspect of the present invention, there is provided a deodorant composition comprising ethylhexylglycerol, triethyl citrate and BHT, wherein the ratio of ethylhexylglycerol to triethyl citrate is from 1:6 to 1:1 by weight and wherein the ratio of BHT to the sum of ethylhexylglycerol and triethyl citrate is from 1:40 to 1:5 by weight.

We have surprisingly discovered that by topical application of a composition according to the first aspect of the invention a significant deodorancy benefit can be delivered to the human body.

In a second aspect of the present invention, there is provided a non-therapeutic method of reducing body odour comprising the topical application of a composition according to the first aspect of the invention to the human body.

Without wishing to be bound by theory, it is believed that the deodorancy benefit delivered by the present invention is obtained primarily by an anti-microbial action upon the skin microflora. In particular, it is hypothesised that bacteria responsible for the conversion of secretions from the eccrine and/or apocrine glands into malodorous materials are reduced by use of the present invention.

DETAILED DESCRIPTION

The method of controlling malodour offered by the present invention is particularly useful because the benefit can extend for many hours, for example 10 hours, 24 hours, or even longer, after application of the product. This can represent an extended deodorancy benefit; that is to say, extended inhibition of the generation of odour on the human body or closely associated articles.

The method of achieving an anti-microbial and deodorancy benefit of the present invention is most efficacious when it comprises topical application of the composition directly to the human body. It is further preferred that the composition is sprayed onto the surface of the human body.

The composition of the invention may be applied to the human body by any means. Application of liquid compositions may be by absorption onto a carrier matrix like paper, fabric, or sponge and application by contacting said carrier matrix with the surface of the body. Solid or semi-solid compositions may be applied by direct contact or may be dissolved or dispersed in a liquid medium prior to application. Application may also comprise a combination of any two or more of the above techniques.

Essential ingredients of compositions of the present invention are ethylhexylglycerol, triethyl citrate and BHT.

Herein, "ethylhexylglycerol" is sometimes abbreviated to EHG and is 3-(2-ethylhexyl)glycerol, also known as ethylhexylglycerin and octoxyglcerin. It has the IUPAC name 3-[(2-ethylhexyl)oxy]-1,2-propanediol.

Herein, "triethylcitrate" is sometimes abbreviated to TEC and is the triethyl ester of citric acid. It has IUPAC name 1,2,3-triethyl 2-hydroxypropane-1,2,3-tricarboxlate.

Herein, "BHT" is butylated hydroxytoluene, also known as dibutylhydroxytoluene and having the IUPAC name 2,6-bis(1,1-dimethylethyl)-4-methylphenol.

Herein, all amounts, percentages and ratios are by weight, unless otherwise indicated. In addition, all percentages are by weight of the total composition.

Herein, all amounts, percentages and ratios are to be understood as prefixed by the word "about".

Herein, "volatile propellant" means a gas capable of being liquefied by compression and having a boiling point of less than 10° C. and preferably less than 0° C.

Herein, any material, ratio or weight indicated as "preferred" is to be understood as preferably used in combination within any other material, ratio or weight indicated as "preferred".

Herein, the word "comprising" and "comprised of", etc., should be understood as meaning that other components/features could also be present; i.e. the listed steps or options need not be exhaustive.

The ratio of ethylhexylglycerol to triethyl citrate is from 1:6 to 1:1, preferably from 1:3 to 1:1 and more preferably from 1:2 to 1:1. These ratios, in combination with the other features of the invention, have been found to give optimum deodorancy performance. Without wishing to be bound by theory, it is hypothesised that anti-microbial performance against a range of odour causing bacteria is optimised within these ranges.

The ratio of BHT to the sum of ethylhexylglycerol and triethyl citrate is from 1:40 to 1:5, preferably from 1:30 to 1:10 and more preferably from 1:20 to 1:10. These ratios, in combination with the other features of the invention, have been found to give optimum deodorancy performance. Without wishing to be bound by theory, it is hypothesised that anti-microbial performance against a range of odour causing bacteria is optimised within these ranges.

The ethylhexylglycerol used in the present invention is preferably employed at a level of from 0.2 to 2%, more preferably at from 0.2 to 1.5% and most preferably at from 0.3 to 1%.

The triethyl citrate used in the present invention is preferably employed at a level of from 0.3 to 3%, more preferably at from 0.6 to 2% and most preferably at from 0.75 to 1.5%.

A particularly preferred combination is ethylhexylglycerol at from 0.3 to 1% and triethyl citrate at 0.75 to 1.5, especially when the ratio of ethylhexylglycerol to triethyl citrate is from 1:2 to 1:1.

The BHT used in the present invention is preferably employed at a level of from 0.05 to 0.5%, more preferably at from 0.075 to 0.25% and most preferably at from 0.09 to 0.15%.

Optional Additional Components

A fragrance is a highly preferred additional component in compositions according to the present invention. The presence of a fragrance may enhance the deodorancy benefit delivered, whether by a masking effect or otherwise and may lead to a synergistic enhancement of the deodorancy benefit.

Herein, the terms "fragrance" and "perfume" are used interchangeably and can refer to single fragrance or perfume accords or multiple such accords.

When a fragrance is used, it may be in the form of a free (non-encapsulated) fragrance, optionally emulsified, or it may be encapsulated in one of the multiple encapsulating materials used for this purpose. Encapsulated fragrances are a preferred feature of compositions of the invention, especially in compositions also comprising a non-encapsulated fragrance. Compositions of the invention including both encapsulated and non-encapsulated fragrance can deliver enhanced, long-lasting deodorancy.

Fragrance may be advantageously employed at a total level of from 0.1 to 6%, preferably 0.5 to 5% and more preferably at from 1 to 4% by weight of the total composition, excluding any volatile propellant that may be present therein.

A liquid carrier fluid is a highly desired additional component of the products of the invention. The carrier fluid may be hydrophobic or hydrophilic. Hydrophobic liquids suitable for use with the invention include silicones oils, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, or additionally, non-silicone hydrophobic liquids may be used. Such materials include mineral oils, hydrogenated polyisobutene, polydecene, paraffins, isoparaffins of at least 10 carbon atoms, aliphatic or aromatic ester oils (eg. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers.

Particular preferred carrier fluids comprise silicone oil, particularly when also comprising an ester oil and especially when comprising an ester oil and an ether oil.

Particular preferred carrier fluids comprise an ester oil and/or an ether oil, particularly when also comprising a silicone oil.

The choice of preferred components and/or combinations of components in the carrier fluid may enhance the deodorancy performance of the composition, by enhanced spreading of the deodorant active system on the surface of the human body or by other means.

Mixtures of carrier materials may also be used. The amount of carrier material employed is preferably at least 5%, more preferably from 30% to 99%, and most preferably from 60% to 98% by weight of the composition, excluding any volatile propellant present.

When organic solvent is present in the composition, it is preferably present at from 30% to 98% by weight of the total weight of the liquid components of the composition; more preferably the organic solvent comprises from 60% to 97% by weight of the total liquids present.

For many applications, it is desired that less than 50% by weight of water is present as part of the liquid components of the composition, more preferably less than 10%. For some preferred compositions, the ratio of other liquid components to water is between 95:5 and 99:1, by weight.

Inorganic antimicrobial agents, in particular antiperspirant salts that are aluminium, zirconium and aluminium/zirconium halides and halohydrate salts, are preferably absent from compositions of the present invention. Hence, preferred compositions exclude any aluminium-containing antiperspirant active. The present inventors have found that acceptable deodorancy benefits can be achieved without the use of such astringent materials.

The ethanol content of compositions of the invention is preferably kept to a minimum, by which is meant the level is kept below 1%, preferably below 0.5% and more preferably below 0.1%. Most preferably, ethanol is completely absent from compositions of the invention.

In particularly preferred embodiments, both ethanol and inorganic antimicrobial agents, in particular antiperspirant salts that are aluminium, zirconium and aluminium/zirconium halides and halohydrate salts, are absent.

Structurants and emulsifiers are further additional components of the compositions of the invention that are highly desirable in certain product forms. Structurants, when employed, are preferably present at from 1% to 30% by weight of the composition, whilst emulsifiers are preferably present at from 0.1% to 10% by weight of the composition. Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Suitable emulsifiers include steareth-2, steareth-20, steareth-21, ceteareth-20, glyceryl stearate, cetyl alcohol, cetearyl alcohol, PEG-20 stearate, dimethicone copolyol, and poloxamines.

Further emulsifiers/surfactants desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers.

Certain sensory modifiers are further desirable components in the compositions of the invention. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (eg. Aerosil 200), polyethylene (eg. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Preferred compositions of the invention are aerosol compositions having a volatile propellant present as an essential component. The level of incorporation of the volatile propellant is typically from 30 to 99 parts by weight, and particularly from 50 to 95 parts by weight.

Non-chlorinated volatile propellants are preferred, in particular liquefied hydrocarbons or halogenated hydrocarbon gases (particularly fluorinated hydrocarbons such as 1,1-difluoroethane and/or 1-trifluoro-2-fluoroethane). It is especially preferred to employ liquefied hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

EXAMPLES

The materials detailed in Table 1 were used in the compositions detailed below.

The aerosol compositions detailed in Table 2 were prepared by methods known in the art. In order to assess the antimicrobial performance of the compositions, the following procedure was performed.

TABLE 1

| Abbreviated name | INCI name | Trade name | Supplier |
| --- | --- | --- | --- |
| Ester oil | C12-15 alkyl benzoate | Finsolv TN | Finnex |
| Silicone oil | Cylcomethicone | DC 245 | Dow Corning |
| Ether oil | PPG-14 Butyl Ether | Fluid AP | Dow Chemicals |
| Propellant | Butane, isobutane, propane | CAP40 | BOC |
| Bentone | Disteardimonium hectorite | Bentone 38V | Elementis |
| PC | Propylene carbonate | Propylene carbonate | ISP |

Pigskin was obtained from a local butcher, cleaned, cut into 4 cm×4 cm pieces, sterilised by □-irradiation, and stored at −20° C. until required. Pigskin pieces were allowed to thaw overnight in a fridge, then transferred to individual sterile petri dishes containing moistened tissues. The pieces were gently swabbed with 96% ethanol and the petri dishes were warmed in an incubator at 35° C. and held until ready for use. Meanwhile, *Staphylococcus epidermidis* ATCC 12228 was grown in TSBT broth (30 g/l Tryptone soy broth; 10 g/l Yeast extract; 1 g/l Tween 80), harvested by centrifugation, and re-suspended in sterile phosphate-buffered saline (PBS). Using a spectrophotometer, the turbidity was adjusted to an optical density of 0.25 with PBS, equivalent to ~$10^8$ colony-forming units (CFU) per ml. Each pigskin piece was inoculated with a suspension of *S. epidermidis* (200 µl) and the cells were evenly distributed using a sterile spreader. Petri dishes containing the inoculated pigskin pieces were placed in an incubator for 1 hr. at 35° C.

The deodorant aerosol compositions detailed in Table 2 were applied minus the propellant, i.e. as base compositions, to pigskin pieces at a dose of 2.6 mg/cm². Following inoculation and treatment with product, samples were taken from the skin surface immediately and again after 5 hr. incubation at 35° C. Sampling was performed using sterile scrub cups (2 cm diameter) consisting of a Teflon cylinder and Teflon rod. The cylinder was held tightly against the skin surface and aliquots (0.75 ml) of quench fluid (PBS; 0.3% Lecithin; 0.5% sodium thiosulphate; 0.1% L-histidine; 3% Tween 80) pipetted within. The skin surface was agitated by means of the Teflon rod and this procedure was carried out twice for 30 s each, and the retained fluids pooled. Serial dilutions of the buffer scrubs were made in sterile diluent (1 g/l Peptone; 8.5 g/l sodium chloride) and plated on TSAT agar (30 g/l Tryptone soy broth; 10 g/l Yeast extract; 1 g/l Tween 80; 20 g/l Agar No. 1) for colony counting. The log reduction in *S. epidermidis* for each deodorant base was calculated by comparing recovered bacterial numbers for the product and an untreated control after 5 hr.

The results for Examples 1, 3 and 4 indicated a reduction in bacterial numbers of at least two orders of magnitude. The result for Example 2 was marginally less at 1.92 orders of magnitude.

TABLE 2

| | Example | | | | |
| --- | --- | --- | --- | --- | --- |
| | 1 | 2 | 3 | 4 | A |
| Ester oil | 1.00 | 1.00 | 1.00 | 1.00 | 1.00 |
| Silicone oil | 1.85 | 1.45 | 0.95 | 2.95 | 3.95 |
| Ether oil | 1.95 | 1.00 | 1.00 | 1.00 | 1.00 |
| Octyldodecanol | 0.10 | 0.10 | 0.10 | 0.10 | 0.10 |
| SSO | 0.50 | — | — | — | — |
| EHG | 1.00 | 0.50 | 1.00 | 1.00 | 1.00 |
| TEC | 1.00 | 3.00 | 3.00 | 1.00 | — |
| BHT | 0.10 | 0.10 | 0.10 | 0.10 | 0.10 |
| Bentone | — | 0.30 | 0.30 | 0.30 | 0.30 |
| PC | — | 0.04 | 0.04 | 0.04 | 0.04 |
| Fragrance | 1.50 | 1.25 | 1.25 | 1.25 | 1.25 |
| Fragrance encapsulates | — | 0.36 | 0.36 | 0.36 | 0.36 |
| Propellant | To 100 | To 100 | To 100 | To 100 | To 100 |
| Result: | 2.07 | 1.92 | 2.41 | 2.11 | 1.13 |

Comparative Example A, which lacked TEC, gave a significantly poorer reduction in bacterial numbers.

The aerosol composition detailed in Table 3 was prepared by methods known in the art and filled into a conventional deodorant aerosol dispenser.

TABLE 3

| | Example 5 |
| --- | --- |
| Ester oil | 1.00 |
| Silicone oil | 1.60 |
| Ether oil | 1.00 |
| EHG | 0.50 |
| TEC | 3.00 |
| BHT | 0.10 |
| Bentone | 0.30 |
| PC | 0.04 |
| Fragrance | 1.10 |
| Fragrance encapsulates | 0.36 |
| Propellant | To 100 |

The deodorancy performance of Example 5 was evaluated using the following protocol.

A panel of 50 male panellists was employed. At the start of the test, panellists were washed with unfragranced soap and different treatments applied to each axilla: a two second spray of Example 1 (ca. 1.68 g) to one axilla and no treatment to the other. Application was randomised to take into account any left/right bias. Panellists were instructed not to consume spicy food or alcohol, and not to wash under their own axillae, during the duration of the test. At least three expert assessors determined the intensity of axillary odour after 24 hours, scoring the intensity on a scale of 0-5 (where 0=no odour). Two further repeat cycles were performed. At the end of the test, the data were analysed using standard statistical techniques.

It was found that treatment with Example 5 led to an average odour score of 1.78, whereas the "no treatment" control led to an average odour score of 2.24. This difference was significant at the 99% level of confidence.

The invention claimed is:

1. A deodorant composition comprising ethylhexylglycerol, triethyl citrate and BHT, wherein the ratio of ethylhexylglycerol to triethyl citrate is from 1:6 to 1:1 by weight, wherein the ratio of BHT to the sum of ethylhexylglycerol and triethyl citrate is from 1:40 to 1:5 by weight, and wherein the ratio of other liquid components to water is between 95:5 and 99:1, by weight.

2. A deodorant composition according to claim 1, excluding ethanol.

3. A deodorant composition according to claim 1, excluding any aluminium-containing antiperspirant active.

4. A deodorant composition according to claim 1, wherein the ratio of ethylhexylglycerol to triethyl citrate is from 1:3 to 1:1 by weight.

5. A deodorant composition according to claim 1, wherein the total level of ethylhexylglycerol and triethyl citrate is at least 1% by weight.

6. A deodorant composition according to claim 1, which is an aerosol composition comprising a volatile propellant.

7. A deodorant composition according to claim 1, comprising a liquid carrier fluid.

8. A deodorant composition according to claim 7, wherein the carrier fluid comprises a silicone oil.

9. A deodorant composition according to claim 7, wherein the carrier fluid comprises an ester oil.

10. A deodorant composition according to claim 7, wherein the carrier fluid comprises an ether oil.

11. A deodorant composition according to claim 1, comprising a non-encapsulated fragrance.

12. A deodorant composition according to claim 1, comprising an encapsulated fragrance.

13. A method of reducing malodour on the surface of the human body, comprising the topical application of a deodorant composition according to claim 1.

14. A method according to claim 13, wherein the composition is sprayed directly onto the surface of the human body.

* * * * *